(12) United States Patent
Chan

(10) Patent No.: US 7,887,757 B2
(45) Date of Patent: Feb. 15, 2011

(54) METHOD AND APPARATUS FOR DISPENSING DIAGNOSTIC TEST STRIPS

(75) Inventor: Victor Chan, Landing, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 911 days.

(21) Appl. No.: 11/430,178

(22) Filed: May 9, 2006

(65) Prior Publication Data

US 2007/0264165 A1 Nov. 15, 2007

(51) Int. Cl.
*B01L 9/00* (2006.01)

(52) U.S. Cl. .................. 422/104; 422/99; 221/258; 221/259

(58) Field of Classification Search ............. 422/104, 422/99, 102; 221/258–259, 231
See application file for complete search history.

(56) References Cited

U.S. PATENT DOCUMENTS

| 3,269,591 | A | * | 8/1966 | Harter ................... 221/23 |
| 4,324,345 | A | | 4/1982 | Martinez |
| 4,783,056 | A | | 11/1988 | Abrams |
| 4,812,116 | A | | 3/1989 | Abrams |
| 4,911,344 | A | | 3/1990 | Kahler |
| 5,018,614 | A | * | 5/1991 | Ruckert ................ 194/236 |
| 5,280,845 | A | * | 1/1994 | Leight ................... 221/2 |
| 5,489,414 | A | | 2/1996 | Schreiber et al. |
| 5,510,266 | A | | 4/1996 | Bonner et al. |
| 5,632,410 | A | | 5/1997 | Moulton et al. |
| 5,645,798 | A | | 7/1997 | Schreiber et al. |
| 5,720,924 | A | | 2/1998 | Eikmeier et al. |
| 5,723,085 | A | | 3/1998 | Abrams et al. |
| 5,738,244 | A | | 4/1998 | Charlton et al. |
| 5,810,199 | A | | 9/1998 | Charlton et al. |
| 5,854,074 | A | | 12/1998 | Charlton et al. |
| 5,863,800 | A | | 1/1999 | Eikmeier et al. |
| 5,911,937 | A | | 6/1999 | Hekal |
| 6,176,119 | B1 | | 1/2001 | Kintzig |
| 6,213,343 | B1 | | 4/2001 | Damikolas |
| 6,379,317 | B1 | | 4/2002 | Kintzig et al. |
| 6,475,436 | B1 | | 11/2002 | Schabbach et al. |
| 6,497,845 | B1 | | 12/2002 | Sacherer |
| 6,872,358 | B2 | | 3/2005 | Hagen et al. |
| 6,908,008 | B2 | | 6/2005 | Pugh |
| 6,941,948 | B2 | * | 9/2005 | Staniforth et al. ...... 128/203.21 |
| 6,988,996 | B2 | | 1/2006 | Roe et al. |
| 2002/0125628 | A1 | * | 9/2002 | Chen et al. ............... 271/10.12 |

(Continued)

FOREIGN PATENT DOCUMENTS

DE 30 01 332 7/1981

(Continued)

*Primary Examiner*—Michael A Marcheschi
*Assistant Examiner*—Jameson Q Ma
(74) *Attorney, Agent, or Firm*—Roylance, Abrams, Berdo & Goodman, L.L.P.

(57) ABSTRACT

An apparatus for storing and dispensing a test strip includes a container configured to store a stack of test strips. The container maintains appropriate environmental conditions, such as humidity, for storing the test strips. An engaging member is disposed in the container and is adapted to contact one test strip of the stack of test strips. An actuator actuates the engaging member to dispense the one test strip from the container. Since one test strip is dispensed at a time, the remaining test strips are not handled by the user. Accordingly, the unused test strips remain free of contaminants such as naturally occurring oils on the user's hand.

7 Claims, 9 Drawing Sheets

U.S. PATENT DOCUMENTS

| | | |
|---|---|---|
| 2003/0121932 A1 | 7/2003 | Wajda |
| 2005/0017018 A1 | 1/2005 | Von Falkenhausen et al. |
| 2005/0057602 A1* | 3/2005 | Okamoto .................. 347/29 |
| 2005/0082742 A1* | 4/2005 | Kang et al. .............. 271/121 |
| 2007/0215634 A1* | 9/2007 | Levin .................... 221/231 |

FOREIGN PATENT DOCUMENTS

WO    WO 2005/051822    6/2005

* cited by examiner

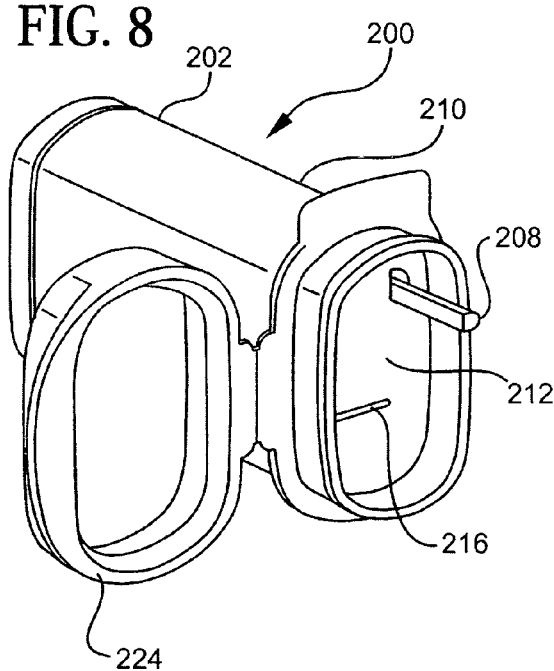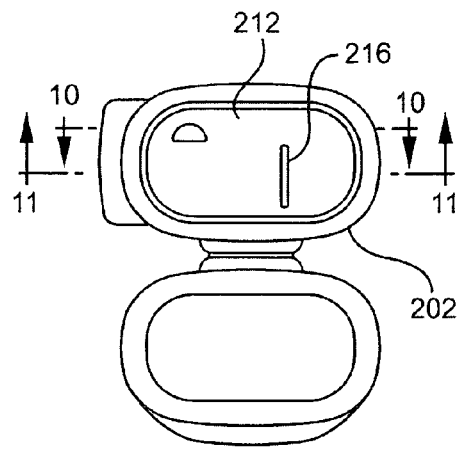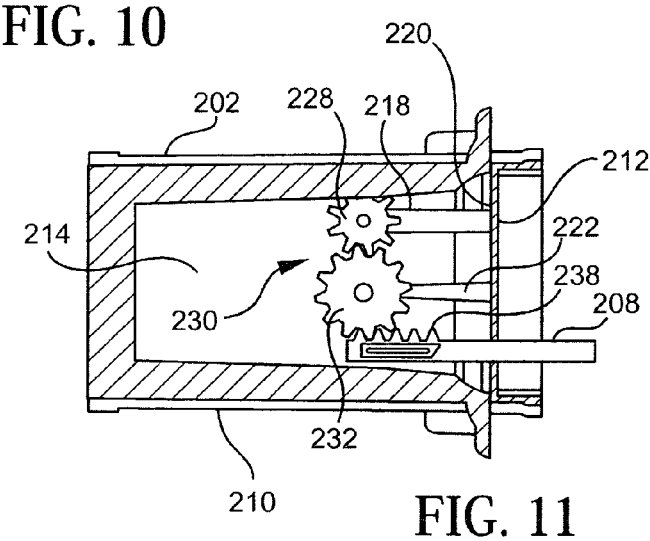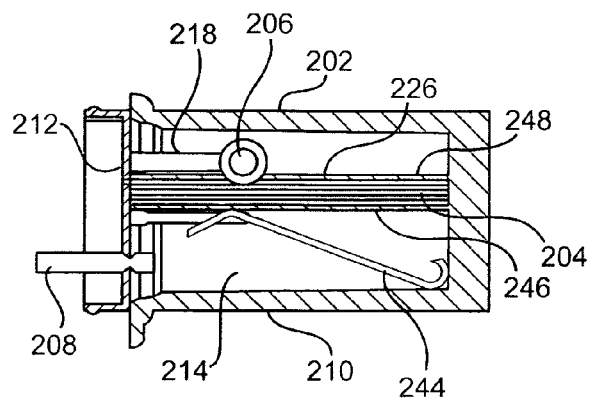

METHOD AND APPARATUS FOR DISPENSING DIAGNOSTIC TEST STRIPS

BACKGROUND OF THE INVENTION

1. Field of the Invention

The present invention generally relates to diagnostic test strips for testing biological fluids. More specifically, the present invention relates to an apparatus and method for storing and dispensing diagnostic test strips.

2. Background of the Invention

Diagnostic test strips are used to measure analyte concentrations in biological fluids. For example, diagnostic test strips are often used by diabetic patients to monitor blood glucose levels.

To preserve their integrity, diagnostic test strips must be maintained in appropriate environmental conditions. That is, the test strips should be maintained at appropriate humidity levels, and should remain free of foreign substances. Furthermore, to avoid contamination by oils or foreign substances, test strips should not be handled prior to use.

Thus, to preserve test strips, they are typically maintained in a storage vial or the like. In order to use the test strip, a user must reach into the vial, and retrieve a single test strip. However, many users, such as diabetic patients, have impaired vision or physical dexterity. Such users may find it difficult to retrieve a single test strip from a storage vial. Further, users may accidentally touch multiple test strips while reaching into the storage vial to withdraw a test strip, and potentially contaminate the unused test strips.

Accordingly, there is a need for an apparatus for storing diagnostic test strips in appropriate environmental conditions, and for conveniently dispensing the test strips one at a time.

SUMMARY OF THE INVENTION

An object of the present invention is to address at least the above problems and/or disadvantages and to provide at least the advantages described below. Accordingly, an object of the present invention is to provide an apparatus for storing a plurality of test strips and for dispensing the test strips one at a time.

According to one embodiment of the present invention, the above and other objects are achieved by an apparatus for storing and dispensing a test strip which comprises a container configured to store a stack of test strips, a roller disposed in the container, the roller adapted to contact one test strip of the stack of test strips, and an actuator for actuating the roller to dispense the one test strip from the container.

According to another embodiment of the present invention, an apparatus for storing and dispensing a test strip comprises a container configured to store a stack of test strips, a lid connected to the container by a living hinge, and a linkage assembly operatively connected to the lid. The linkage assembly is adapted to contact one test strip of the stack of test strips so that when the lid is opened, a test strip is dispensed.

According to yet another embodiment of the present invention, an apparatus for storing and dispensing test strips comprises a container configured to store a stack of test strips, a spring disposed in the container, the spring adapted to contact one test strip of the stack of test strips, and an actuator for actuating the spring to dispense the one test strip from the container.

According to still another embodiment of the present invention, an apparatus for storing and dispensing test strips comprises means for storing a stack of test strips, means for contacting one test strip of the stack of test strips, and means for actuating the contacting means to dispense the contacted test strip.

According to a still further embodiment of present invention, a method of storing and dispensing test strips comprises the steps of arranging a plurality of test strips to form a stack of test strips, storing the plurality of test strips in a storage container, urging the stack of test strips toward a dispensing position, engaging the stack of test strips with an engaging member, actuating the engaging member to dispense the contacted test strip, and urging the remaining test strips toward the dispensing position so that another test strip is placed into a dispensing position.

BRIEF DESCRIPTION OF THE DRAWINGS

The above and other objects, features, and advantages of certain exemplary embodiments of the present invention will be more apparent from the following description taken in conjunction with the accompanying drawings, in which:

FIG. 8 is a perspective view of a storage vial for storing and dispensing test strips according to a second exemplary embodiment of the present invention;

FIG. 9 is a top view of the storage vial shown in FIG. 8;

FIG. 10 is a sectional view taken along the line 10-10 in FIG. 9;

FIG. 11 is a sectional view taken along the line 11-11 in FIG. 9;

Throughout the drawings, the same reference numerals will be understood to refer to the same elements, features and structures.

DETAILED DESCRIPTION OF EXEMPLARY EMBODIMENTS

Figure 1:
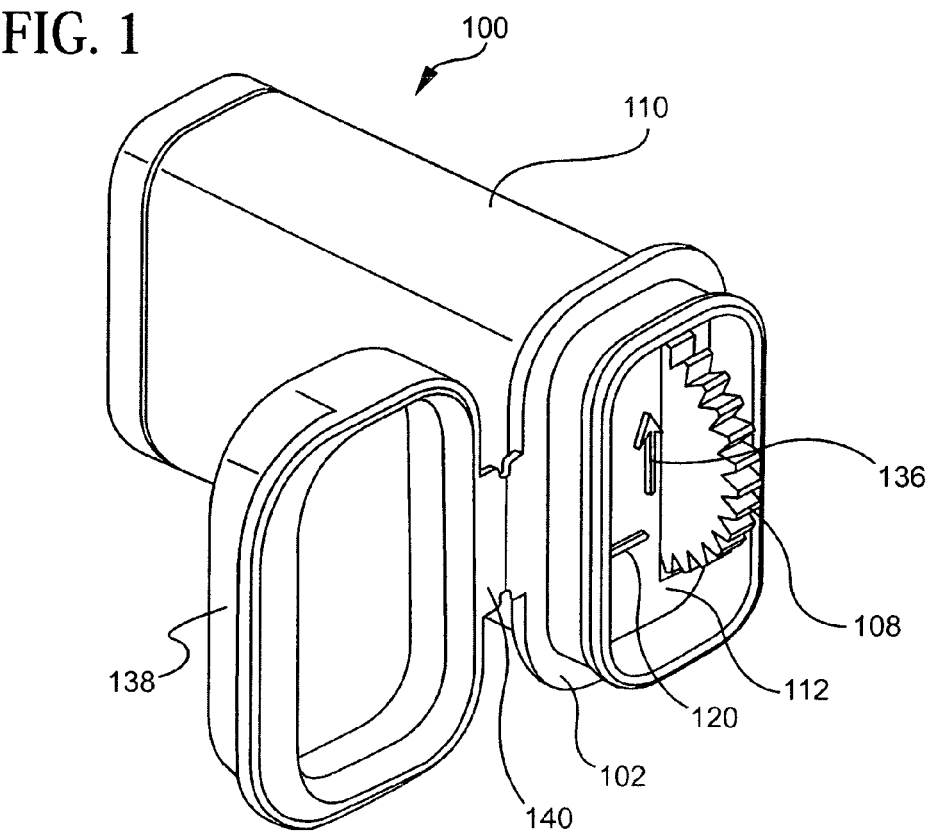
FIG. 1 is a perspective view of a storage vial for storing and dispensing test strips, according to a first exemplary embodiment of the present invention.
Figure 2:
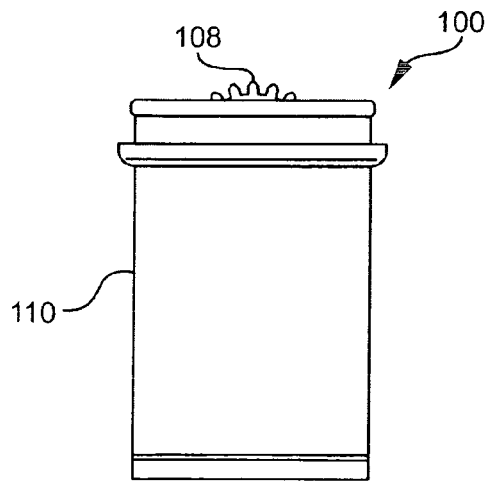
FIG. 2 is a front view of the storage vial shown in FIG. 1.
Figure 3:
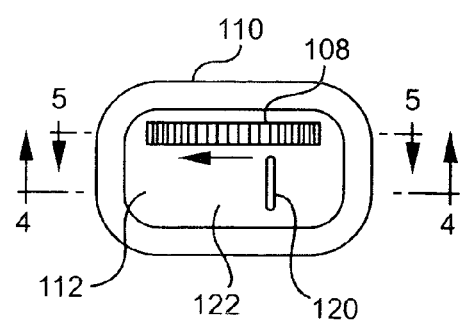
FIG. 3 is a top view of the storage vial shown in FIG. 1.
Figure 4:
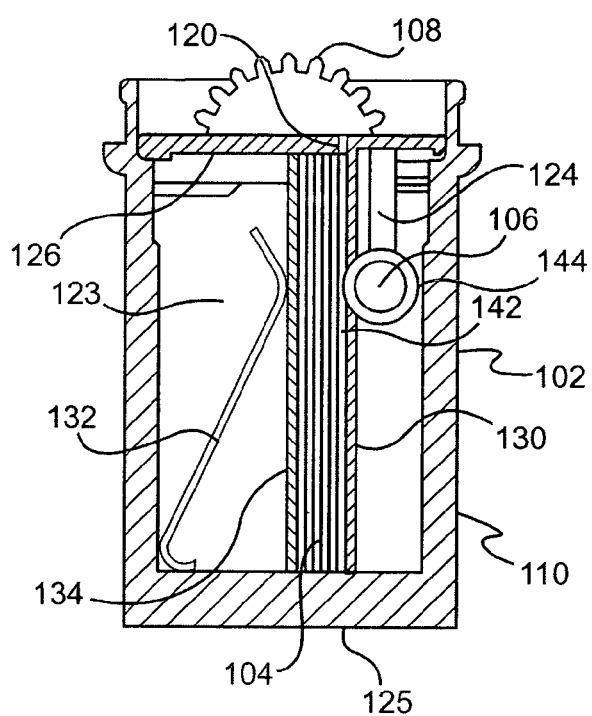
FIG. 4 is a sectional view taken along the line 4-4 in FIG. 3.
Figure 5:
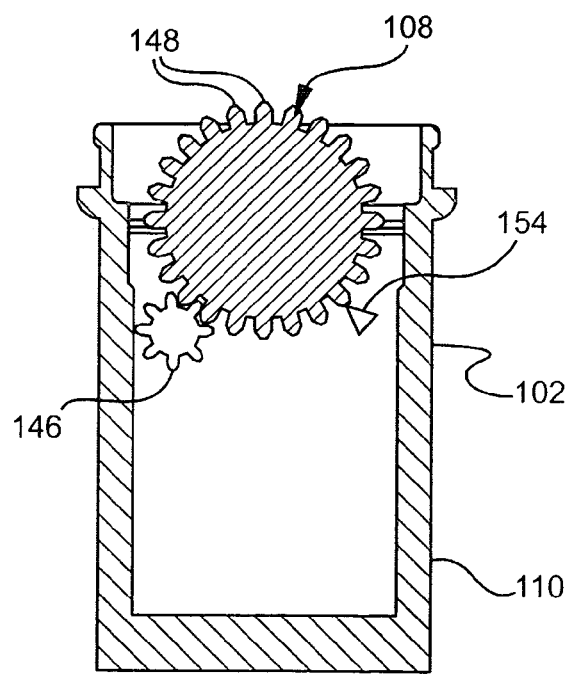
FIG. 5 is a sectional view taken along the line 5-5 in FIG. 3.
Figure 6:
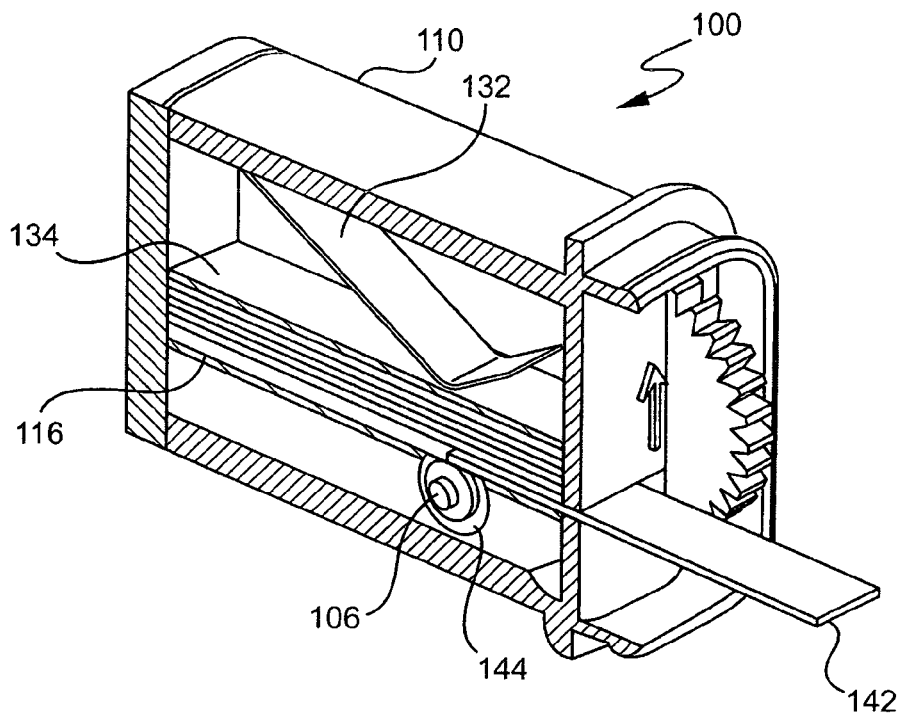
FIG. 6 is a partially cut-away perspective view of the storage vial shown in FIG. 1, with a test strip partially dispensed.

The matters defined in the description such as detailed construction and elements are provided to assist in a comprehensive understanding of the embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

First Exemplary Embodiment

Referring to FIGS. 1-7, a storage vial 100 for storing and dispensing test strips according to a first exemplary embodiment of the present invention includes a storage container 102 configured to store a stack of test strips 104, a strip roller 106 rotatably disposed in the container, and a thumbwheel 108 rotatably disposed in the container. The strip roller 106 contacts one test strip 142 of the stack of test strips 104. The thumbwheel 108 operates the strip roller 106 so that when the thumbwheel 108 is rotated, the strip roller 106 rotates to dispense the test strip 142 in contact with the strip roller 106.

The storage container 102 includes a lower body portion 110 and a top wall 112 mounted in the lower body portion 110. The lower body portion 110 of the storage container 102 is generally rectangular and forms a cavity 123 which is configured to store a stack of test strips 104. A test strip supporting wall 116 extends upwardly from the bottom wall 118 of the container. The test strip supporting wall 116 is tall enough to provide support for the stack of test strips 104 loaded in the storage container 102. The test strip supporting wall 116 may end short of the strip roller 106 so that it does not interfere with the strip roller 106. Alternatively, the test strip supporting wall may extend to the bottom surface of the top wall 112 of the storage container 102, and have an elongated slot to provide clearance for installation and operation of the strip roller 106 (refer to element 331 in FIG. 14).

The storage container 102 may be formed of a desiccant entrained polymer to regulate the specific relative humidity inside the container. U.S. Pat. No. 5,911,937, which is hereby incorporated by reference in its entirety, discloses one suitable desiccant entrained polymer. Alternatively, the storage container 102 may be formed of a polymer with an insert-molded desiccant, or a desiccant may be placed in the cavity 123.

The top wall 112 of the storage container 102 is preferably formed separately from the remainder of the storage container 102 for easier manufacturing and assembly. After the test strips 104 are loaded into the storage container 102, the top wall 112 may be fixed to the storage container 102 by ultrasonic welding, by an adhesive, by mechanical engagement (such as a snap-fit), or by any other suitable method known to those skilled in the art. The top wall 112 of the storage container 102 forms a dispensing slot 120 through which test strips are dispensed. The top surface 122 of the top wall 112 may bear indicia 136 (such as an arrow) for indicating the direction to rotate the thumbwheel 108 to dispense a test strip. A first supporting member 124 extends from the bottom surface 126 of the top wall 112 to rotatably support the strip roller 106, as will be discussed in detail below. A second supporting member 128 also extends from the bottom surface of the top wall 112. The thumbwheel 108 is rotatably supported by the second supporting member 128, and the thumbwheel 108 extends through a second slot through the top wall 112 of the storage container 102. A downwardly extending test strip supporting wall may be located adjacent to the test strip dispensing slot 120 to support and guide test strips into the dispensing slot 120 while they are being dispensed (refer to element 831 in FIG. 14).

The storage container 102 may be provided with a lid 138 to prevent humidity and other environmental contaminants from entering the storage container 102. The lid 138 may be a separate component, but preferably the lid 138 is connected to the storage container 102 by a hinge 140. In the illustrated embodiment, the lid 138 is formed integrally with the lower body portion 110 of the storage container 102 so that it is connected to the storage container 121 by a living hinge 140. The lid 138 preferably forms a substantially hermetic seal with the lower body portion 110 of the storage container 102. Such seals are known to those skilled in the art, and therefore, a detailed description of the seal will be omitted for conciseness. Also, for convenience of explanation, the lid is only shown in some of the drawings.

A biasing element 132, such as a compression spring or a leaf spring, urges the stack of test strips 104 stored in the storage container 102 into contact with the strip roller 106. A platform 134 may be disposed between the biasing element 132 and the stack of test strips 104 to uniformly distribute the force generated by the biasing element 132 along the length of the stack of test strips 104. If the test strips are sufficiently rigid, however, the biasing element 132 may directly contact the test strips.

The strip roller 106 is rotatably supported by the first supporting member 124, which extends downwardly from the top wall 112 of the storage container 102. The strip roller 106 contacts one of the test strips 142 in the stack of test strips 104. In the illustrated embodiment, (FIG. 4), the strip roller 106 engages the right-most test strip 142. Preferably, the strip roller 106 engages the test strip in the upper portion of the test strip. The outer circumferential surface 144 of the strip roller 106 should have a sufficient coefficient of friction to frictionally engage and dispense a test strip. For example, the strip roller 106 may be formed of rubber bonded to a metal or molded plastic roller insert. A strip roller gear 146 is located on one side of the strip roller 106.

A thumbwheel 108 is rotatably supported by the second supporting member 128. A plurality of gear teeth 148 are located around the outer circumference of the thumbwheel 108, and the gear teeth 148 on the thumbwheel 108 engage the strip roller gear 146. The gear teeth 148 also provide friction to allow a user to more conveniently operate the thumbwheel 108 with a thumb, a finger, or the like.

Figure 7:
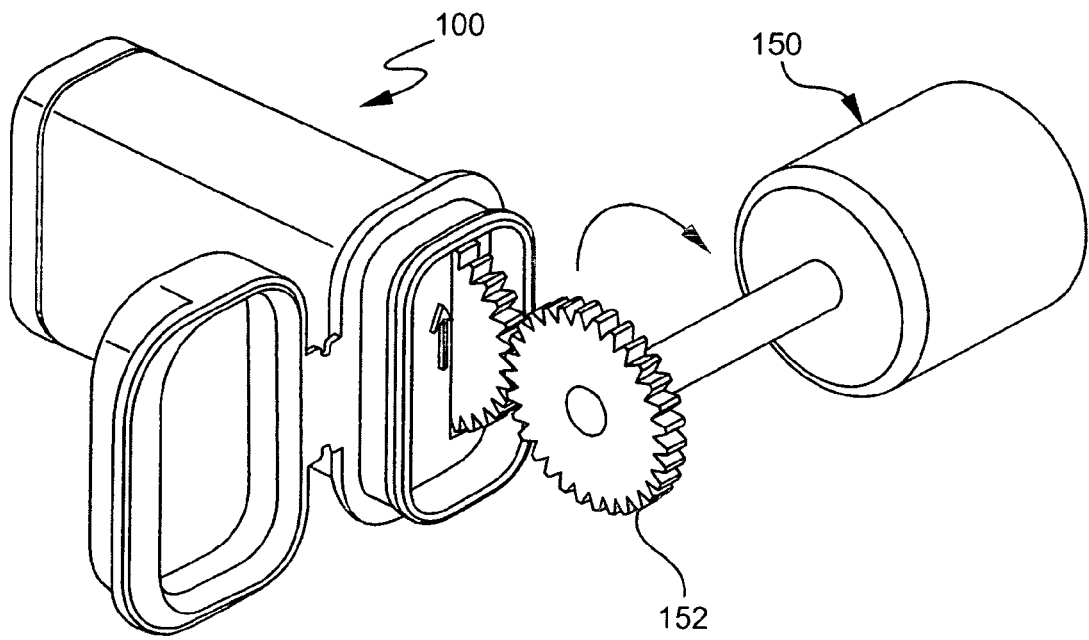
FIG. 7 is a perspective view of the storage vial shown in FIG. 1, with a motor for operating the dispenser.
Figure 12:
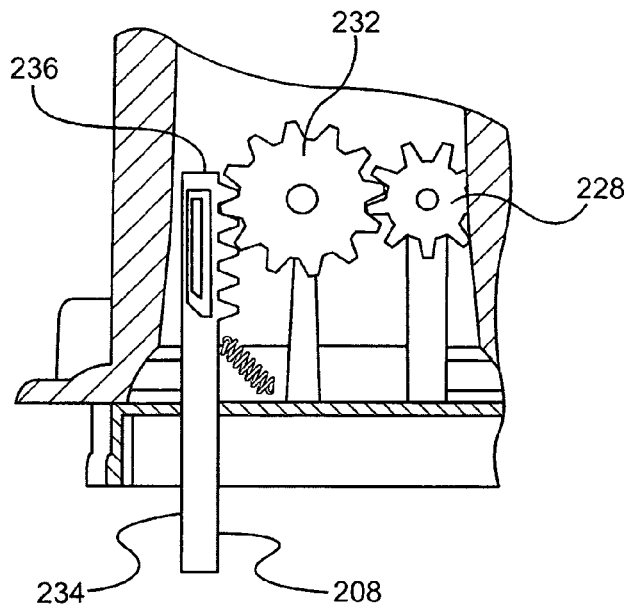
FIG. 12 is an enlarged sectional view of certain elements of the storage vial shown in FIG. 8.

Alternatively, as illustrated in FIG. 7, the storage container 102 may be used in a fully automated test strip dispenser. In this case, the automated test strip dispenser is provided with a motor 150 with a pinion gear 152, and the storage container 102 is disposed in the automated test strip dispenser so that the pinion gear 152 engages the thumbwheel 108. The automated test strip dispenser can, if desired, be combined with a blood glucose meter that reads the test strips 104.

Furthermore, a locking member 154, such as a ratchet or pawl, may be disposed on the storage container 102 to engage the thumbwheel 108. The locking member 154 allows the thumbwheel 108 to rotate in one direction (that is, a dispensing direction), but prevents the thumbwheel 108 from rotating in the opposite direction.

The method of using the storage vial for storing and dispensing test strips according to the first exemplary embodiment of the invention will now be described. Initially, the strip roller 106 and the thumbwheel 108 are assembled to the first and second supporting members 124, 128, respectively, on the top wall 112 of the storage container 102. A stack of test strips 104 is loaded into the lower body portion 110 of the storage container 102 so that the stack of test strips 104 is disposed between the platform 132 and the test strip supporting wall 130. The biasing element 132 is installed in the cavity 123 between the platform 132 and the opposite wall of the storage container. The top wall 112, with the strip roller 106 and the thumbwheel 108 installed, is then assembled to the lower body of the storage container 102. The lid 138 is placed on the storage container 102 to form a substantially hermetic seal. The storage vial 100 may now be stored, and the stack of test strips 104 will be protected from environmental hazards, such as moisture. Typically, these steps will be performed by a manufacturer, rather than an end user of the storage vial.

To dispense a test strip, a user opens the lid 138 to expose the thumbwheel 108 and the strip dispensing slot 120. The user then rotates the thumbwheel 108 in the dispensing direction by manipulating the thumbwheel 108, with the user's fingers or the like. Upon rotation of the thumbwheel 108, the thumbwheel 108 transmits the rotational force to the strip roller 106 through the gear teeth 148 on the thumbwheel 108 and the strip roller gear 146. Therefore, the strip roller 106 rotates. The strip roller 106 contacts one test strip 142 of the stack of test strips 104, and through frictional force generated between the strip roller 106 and the contacted test strip 142, dispenses the contacted test strip 142 through the test strip dispensing slot 120. The thumbwheel 108 may be rotated so that the test strip 142 is completely dispensed out of the storage container 102, or the test strip 142 may be partially dispensed from the storage container 102 to expose the test strip so that a user may grasp the exposed test strip 142 to completely withdraw the test strip and use the test strip.

Once the test strip is completely dispensed from the storage container 102, the biasing element 132 urges the remaining test strips in the stack of test strips 104 toward the strip roller 106 so that a new test strip is placed into contact with the strip roller 106. Thus, to dispense another test strip, the user rotates the thumbwheel 108 again. After dispensing the desired number of test strips, the user may then replace the lid on the storage container 102 to store the remaining test strips for future use.

After all of the stored test strips stored in the storage container 102 have been dispensed, the storage vial 100 may be discarded, or may be returned to the manufacturer for recycling. Alternatively, the storage container 102 may be adapted to be reusable (e.g., by making the top wall 112 removable from the lower body portion 110).

Second Exemplary Embodiment

Referring to FIGS. 8-12, a storage vial 200 for storing and dispensing test strips according to a second exemplary embodiment of the present invention includes a storage container 202 configured to store a stack of test strips 204, a strip roller 206 rotatably disposed in the storage container 202, and a pushbutton 208 disposed in the container. The strip roller 206 contacts one test strip 226 of the stack of test strips 204. The pushbutton 208 is connected with the strip roller 206 by a gear train 230 so that when the pushbutton 208 is pushed, the strip roller 206 rotates to dispense the test strip 226 in contact with the strip roller.

The storage container 202 includes a lower body portion 210 and a top wall 212 mounted in the lower body portion 210. The lower body portion 210 of the storage container 202 is configured substantially the same as the lower body portion 110 of the storage container 100 of the first exemplary embodiment of the invention. Accordingly, a detailed description of the lower body portion 210 will not be repeated.

The top wall 212 of the storage container 202 has a test strip dispensing slot 216 through which test strips are dispensed. A first supporting member 218 extends from the bottom surface 220 of the top wall 212 to rotatably support the strip roller 206, as will be discussed in detail below. A second supporting member 222 extends from the bottom surface 220 of the top wall 212 to rotatably support an intermediate gear 232.

The pushbutton 208 has a first end 234 and a second end 236. The first end 234 of the pushbutton 208 extends through a slot located in the top wall 212 of the storage container 202 so that it may be manipulated by a user. The second end 236 of the pushbutton 208 is disposed inside the cavity 214 of the storage container 202. A rack gear 238 is formed along the length of the pushbutton 208 near the second end 236 of the pushbutton 208.

The pushbutton is movable between a resting position (illustrated in FIG. 10, for example) and a dispensing position. A biasing element 240, such as an extension spring, is disposed between the top wall 212 and the pushbutton 208. The biasing element 240 urges the pushbutton 208 toward the resting position.

The pushbutton 208 has at least one track 242 located on one side of the pushbutton, and may have tracks located on both sides of the pushbutton 208. The tracks 242 are configured to guide the movement of the pushbutton 208 so that when the pushbutton 208 is pressed to dispense a test strip, the rack gear 238 on the pushbutton 208 engages the intermediate gear 232. When the pushbutton 208 is released, the tracks 242 are configured to cause the rack gear 238 to disengage from the intermediate gear 232. Therefore, the pushbutton 208 may be restored from the dispensing position to the resting position without rotating the intermediate gear 238.

The intermediate gear 232 is rotatably disposed on the second supporting member 222 which extends downwardly from the bottom surface 220 of the top wall 212 of the storage container 202. The intermediate gear 232 is disposed between the rack gear 238 on the pushbutton 208 and the strip roller gear 228 on the strip roller 206 to operatively connect the gears and form a gear train 230.

The strip roller 206 is rotatably supported by the first supporting member 218, which extends downwardly from bottom surface 220 of the top wall 212 of the storage container 202. The strip roller 206 is generally configured the same as the strip roller 106 of the first exemplary embodiment of the present invention. Accordingly, a detailed description of the strip roller 206 will not be repeated.

The method of using the storage vial 200 for storing and dispensing test strips according to the second exemplary embodiment of the invention will now be described. Initially, the strip roller 206, the pushbutton 208, the biasing element 240, and the intermediate gear 232 are assembled to the top wall 212 of the storage container 202. A stack of test strips 204 is loaded into the lower body portion 210 of the storage container 202 so that the stack of test strips 204 is disposed between the platform 246 (and the biasing element 232) and the test strip supporting wall 224. The top wall 212, with the installed components, is then assembled to the lower body portion 210 of the storage container 202 so that the strip roller 206 engages one test strip 226 of the stack of test strips 226. The lid 224 may then be closed, and the stack of test strips may be stored as long as desired.

To dispense a test strip, a user opens the lid 224, and pushes the pushbutton 208 to move the pushbutton 208 from a resting position to a dispensing position. Initially, the tracks 242 on the pushbutton 208 cause the rack gear 238 to engage the intermediate gear 232. Consequently, movement of the pushbutton 208 causes the rack gear 238 to rotate the intermediate gear 232. The rotation of the intermediate gear 232 rotates the strip roller gear 228 and causes the strip roller 206 to dispense the test strip 226 which the strip roller 206 contacts. The pushbutton 208 may be configured to completely dispense the test strip 226 out of the storage container 202, or the test strip 226 may be partially dispensed from the storage container 202 to expose the test strip so that a user may grasp the exposed test strip 226 to completely withdraw the test strip from the storage container 202.

After the test strip 226 has been dispensed, the biasing element 244 urges the platform 246 and the stack of test strips 204 against the test strip supporting wall 248 so that a new test strip may be dispensed.

When a user releases the pushbutton 108, the configuration of the tracks 242 on the pushbutton cause the pushbutton 208, along with the rack gear 238, to move away from and disengage the intermediate gear 232. Therefore, the pushbutton 208 may be returned to the resting position without rotating the intermediate and strip roller gears 232, 228 in a reverse direction.

Third Exemplary Embodiment

Figure 13:
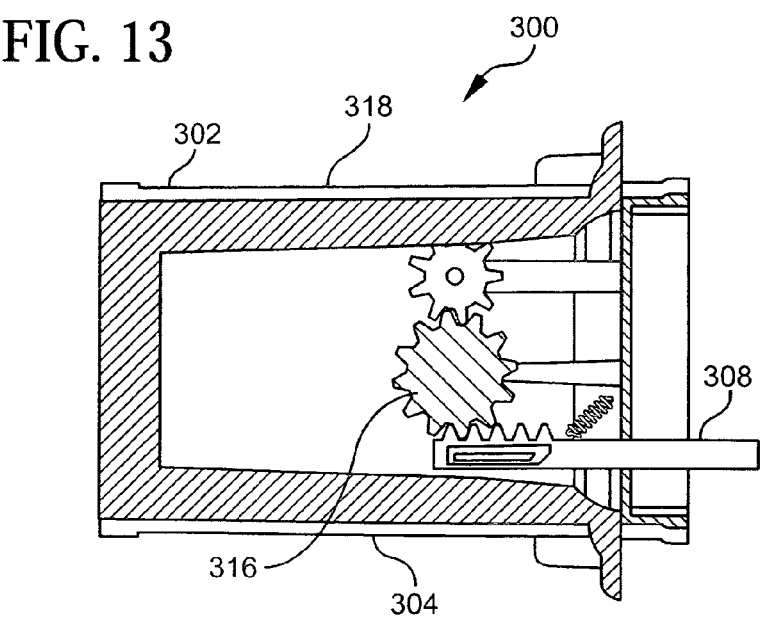
FIG. 13 is a sectional view of a storage vial for storing and dispensing test strips according to a third exemplary embodiment of the present invention.
Figure 14:
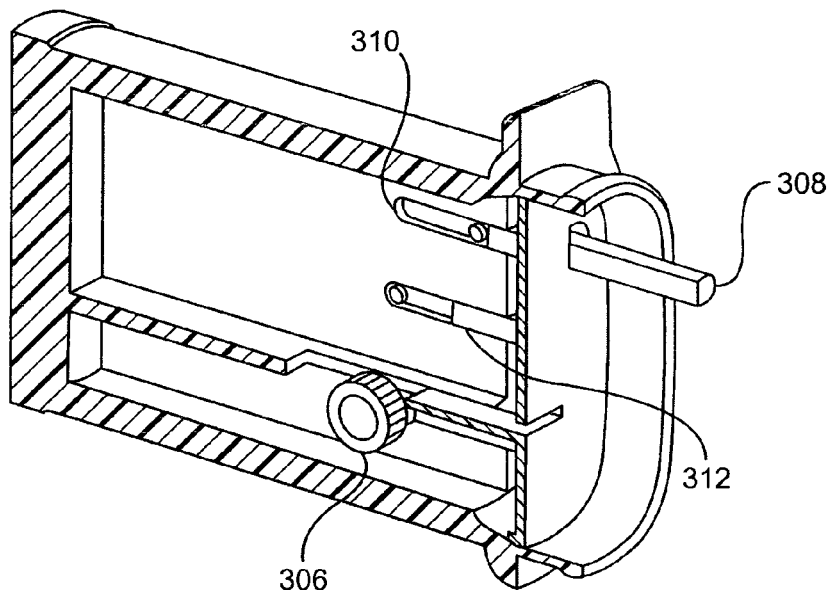
FIG. 14 is another sectional view of the storage vial shown in FIG. 13.

Referring to FIGS. 13-14, a storage vial 300 for storing and dispensing test strips according to a third exemplary embodiment of the present invention includes a storage container 302 configured to store a stack of test strips, a strip roller 306 rotatably disposed in the storage container 302, and a pushbutton 308 disposed in the storage container 302. The strip roller 306 contacts one test strip of the stack of test strips. The pushbutton 308 is connected with the strip roller 306 by a gear train so that when the pushbutton 308 is pushed, the strip roller 306 rotates to dispense the test strip in contact with the strip roller 306.

The storage container 302 of the third exemplary embodiment of the present invention is generally the same as the storage container 202 of the second exemplary embodiment of the present invention, except for the configuration of the intermediate gear 316 of the gear train and the pushbutton 308.

In this embodiment of the invention, the pushbutton 308 does not have tracks for engaging and disengaging the rack gear from the intermediate gear 316. Instead, the pushbutton 308 has extended guide pins (not shown) which are disposed in and guided by pushbutton guide tracks 310 disposed on the inner surface of the outer wall of the lower body portion 304 of the storage container 302. The guide tracks 310 are generally parallel to the edge of the lower body portion so that the pushbutton member moves substantially straight into and out of the storage container 302.

The intermediate gear 316 of this embodiment of the invention is not supported by a supporting member which extends from the top wall of the storage container. Instead, the intermediate gear 316 has extended shaft portions (not shown) which are disposed in and guided by a pair of intermediate gear guide tracks 312 formed on the inner surface of the outer wall of the lower body portion 304 of the storage container 302. Accordingly, the intermediate gear 316 is free to move linearly along the length of the intermediate gear guide tracks 312.

The method of using the storage vial 300 for storing and dispensing test strips according to the third exemplary embodiment of the invention will now be described. Initially, the storage vial 300 is loaded with a stack of test strips and assembled in substantially the same manner described above.

To dispense a test strip, a user pushes the pushbutton 308 to move the pushbutton 308 from a resting position to a dispensing position. Initially, a rack gear on the pushbutton 308 engages the intermediate gear 316, and the intermediate gear 316 moves linearly toward the lower end 314 of the intermediate gear guide tracks 312. Upon reaching the lower end 314 of the intermediate gear guide tracks 312, the guide tracks 312 prevent the intermediate gear 316 from any further linear movement. Accordingly, further movement of the pushbutton 308 causes the rack gear on the pushbutton 308 to rotate the intermediate gear 316. The rotation of the intermediate gear 316 rotates a strip roller gear and causes the strip roller 306 to dispense a test strip. The pushbutton 308 may be configured to completely dispense a test strip, or a test strip may be partially dispensed from the storage container 302 to expose the test strip so that a user may grasp the exposed test strip to completely withdraw the test strip from the storage container 302.

When a user releases the pushbutton 308, a biasing element urges the pushbutton 308 from the dispensing position back to the resting position. During the initial movement of the pushbutton 308 toward the resting position, the intermediate gear 316 translates along the intermediate gear guide tracks 312 to move toward the upper end of the guide tracks. When the intermediate gear 316 moves far enough, it disengages the strip roller gear. Therefore, the pushbutton 308 may be returned to the resting position without rotating the strip roller gear in a reverse direction.

Fourth Exemplary Embodiment

Figure 15:
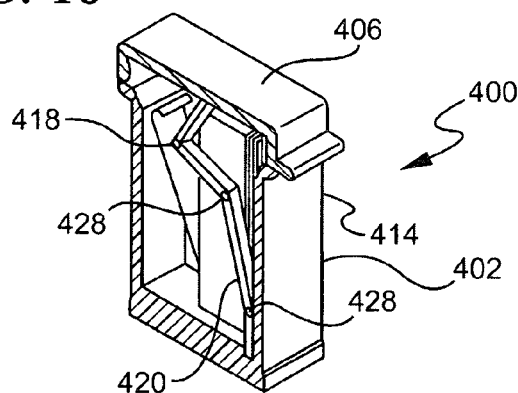
FIG. 15 is a cut-away perspective view of a storage vial for storing and dispensing test strips according to a fourth exemplary embodiment of the present invention.
Figure 16:
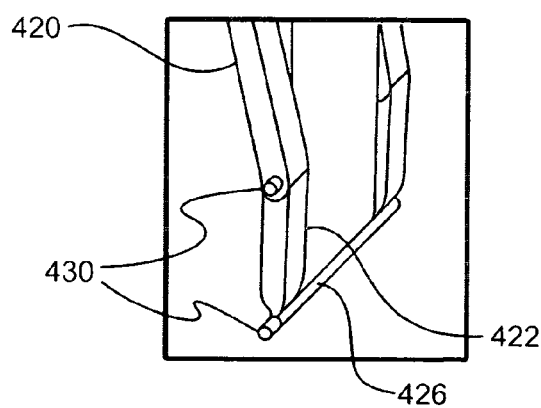
FIG. 16 is an enlarged view of certain elements of the storage vial shown in FIG. 15.
Figure 17:
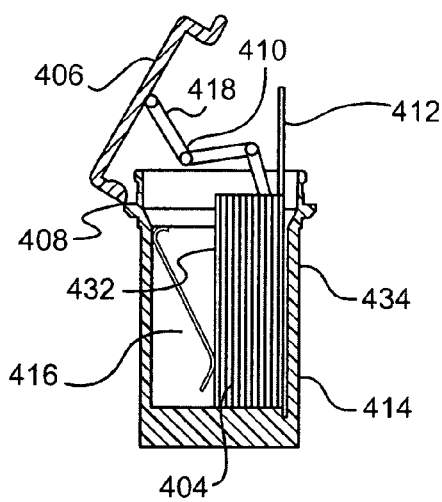
FIG. 17 is a sectional view of the storage vial shown in FIG. 15, with a partially dispensed test strip.

Referring to FIGS. 15-17, a storage vial 400 for storing and dispensing test strips according to a fourth exemplary embodiment of the present invention includes a storage container 402 configured to store a stack of test strips 404, a lid 406 connected to the storage container by a hinge 408, and a linkage assembly 410 operatively connected to the lid 406. When the lid 406 is opened, the linkage assembly 410 engages one test strip 412 of the stack of test strips 404 and dispenses the test strip 412.

The storage container 402 has a generally rectangular lower body portion 414 and forms a cavity 416 which is configured to store a stack of test strips 404. The storage container 402 is formed of any suitable material, as previously discussed.

The storage vial 400 is provided with a lid 406 to prevent humidity and other environmental contaminants from entering the storage container. The lid 406 is connected to the storage vial by a hinge 408. In the illustrated embodiment, the lid 406 is formed integrally with the lower body portion of the storage container so that it is connected by a living hinge 408. Any type of hinge arrangement may be used, however. The lid 406 preferably forms a hermetic seal with the lower body portion 414 of the storage container 402.

The linkage assembly 410 includes a first arm member 418 connected to the lid 406, a second arm member 420 connected to the first arm member 418 by a living hinge 428, and a third arm member 422 connected to the second arm member 420 by a living hinge 428. The first arm member 418 is a generally V-shaped member. The two legs of the V-shaped member form, in the illustrated embodiment, an obtuse angle with respect to one another. The first arm member 418 is attached to the lid 406 by heat staking, by ultrasonic welding, by mechanical attachment, or by any other suitable method known to those skilled in the art.

The second arm member 420 joins the first and third arm members 418, 422 by living hinges 428 at both ends of the second arm. The use of living hinges provide certain benefits, such as lower manufacturing costs, but it should be understood that the arms also may be joined by other types of hinges.

The third arm member 422 has guide members 430, such as guide pins, which are disposed in and configured to travel in rails located in the side wall of the lower body portion 414 of the storage container 402. The third arm member 422 has a lower contacting member 426 which is configured to contact the lower edge of one test strip 412 of the stack of test strips 404. In particular, in the illustrated embodiment, the third arm member 422 contacts the lower edge of the right-most test strip 412.

As illustrated, one set of first, second, and third arm members is provided at the front side of the storage container 402. For stability, a second set of first, second, and third arm members, which is substantially identical to the first set of first, second, and third arm members, may be located at the back side of the storage container 402.

The method of using the storage vial 400 for storing and dispensing test strips according to the fourth exemplary embodiment of the invention will now be described. Initially, the lid 406 is opened, a stack of test strips 404 is loaded into the container between a platform 432 and the outer wall 434 of the storage container 402, and the lid 406 is closed. With the lid 406 closed, the linkage assembly 410 is placed into a resting position. In the resting position, the third arm member 422 is located at the bottom of the storage container, and the lower contacting member 426 is located underneath the bottom edge of the right-most test strip 412.

To dispense a test strip, a user opens the lid 406 of the storage container 402. The opening of the lid 406 causes the first arm member 418 to rotate up and out of the storage container. The second and third arm members 420, 422, which are connected to the first arm member 418, are also raised. The third arm member 422 travels substantially vertically up due to the cooperation of the guide member 430 and the guide rails and is raised up to a dispensing position. Since the lower contacting member 426 of the third arm member 422 is located under a test strip 412, it raises and dispenses the test strip 412. Once the third arm member 422 reaches the dispensing position, a user may grasp the test strip and remove the dispensed test strip 412. The first, second, and third arm members 418, 420, and 422 may be configured to completely dispense the test strip 412 out of the storage container 402, or the test strip 412 may be partially dispensed from the storage container 402 to expose the test strip so that a user may grasp the exposed test strip 412 to completely withdraw the test strip from the storage container 402 and use the test strip.

After the test strip 412 has been dispensed, a user may then close the lid 406. Closing the lid 406 causes the linkage assembly 410 to return to its resting position. When the linkage assembly 410, and the third arm member 422 in particular, reaches the resting position, the biasing element 436 urges the stack of test strips 404 toward the outer wall 434 so that a new test strip is placed over the lower contacting member 426 of the new test strip. Consequently, the storage vial 400 is ready to dispense another test strip.

Fifth Exemplary Embodiment

Figure 18:
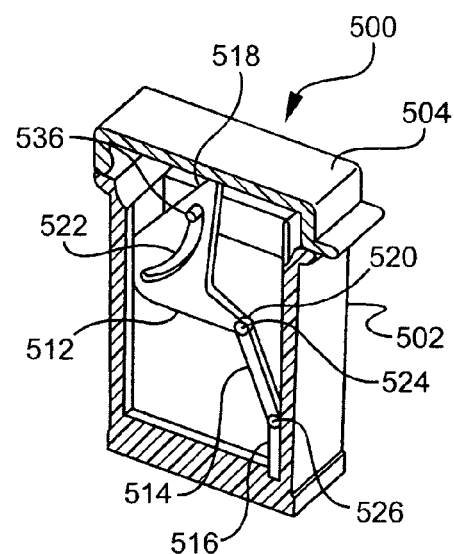
FIG. 18 is a cut-away perspective view of a storage vial for storing and dispensing test strips according to a fifth exemplary embodiment of the present invention.
Figure 19:
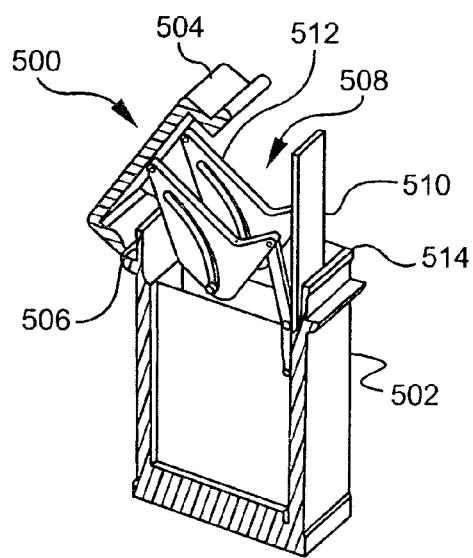
FIG. 19 is a cut-away perspective view of the storage vial shown in FIG. 18, with a partially dispensed test strip.
Figure 20:
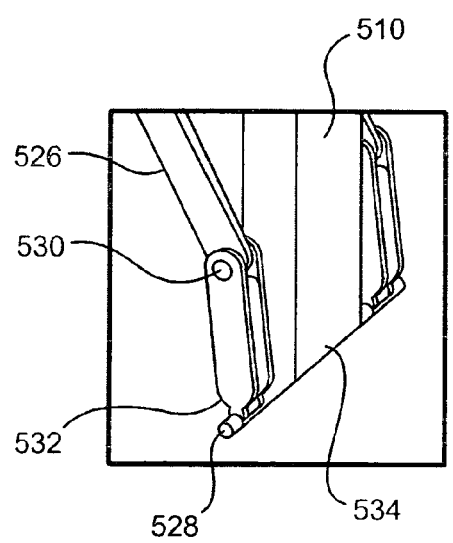
FIG. 20 is a perspective view of a linkage member of the storage vial shown in FIG. 18.

Referring to FIGS. 18-20, a storage vial 500 for storing and dispensing test strips according to a fifth exemplary embodiment of the present invention includes a storage container 502 configured to store a stack of test strips, a lid 504 connected to the storage container 502 by a hinge 506, and a linkage assembly 508 operatively connected to the lid 504. When the lid 504 is opened, the linkage assembly 508 engages one test strip 510 of the stack of test strips and dispenses the test strip.

The storage container 502 and lid 504 of this embodiment is generally configured the same as the storage container 402 and lid 404 of the fourth exemplary embodiment.

The linkage assembly 508 includes at least one slider arm 512, at least one first linkage member 514, and at least one second linkage member 516. In the illustrated embodiment, a pair of slider arms 512, a pair of first linkage members 514, and a pair of second linkage members 516 are provided to increase the stability and reliability of the linkage assembly.

First ends 518 of the slider arms 512 are pivotably connected to the lid 504. Second ends 520 of the slider arms 512 are pivotably connected to the first linkage members 514. Each of the slider arms 512 has a slot 522 that engages a guide boss 536 disposed on the storage container 502.

First ends 524 of the first linkage members 514 are pivotably connected to the second ends 520 of the slider arms 512, and second ends 526 of the first linkage members 514 are pivotably connected to the second linkage members 516.

The second linkage members 516 have guide members 528, such as guide pins, which are disposed in and configured to travel in guide rails located in the side walls of the storage container 502. The first ends 530 of the second linkage members 516 are connected to the second ends 526 of the first linkage members 514. A lower contacting member 534 is disposed between the second ends 532 of the second linkage members 516. The lower contacting member contacts one test strip 510 so that the test strip 510 is dispensed when the lid 504 is opened.

The method of using the storage vial 500 for storing and dispensing test strips according to the fifth exemplary embodiment of the invention will now be described. Initially, the lid 504 is opened, a stack of test strips is loaded into the storage container 502, and the lid 504 is closed. With the lid 504 closed, the linkage assembly 508 is placed into a resting position. In the resting position, the second linkage members 516 are located at the bottom of the storage container 502, and the lower contacting member 534 is located underneath the lower edge of the bottom edge of the right-most test strip 510.

To dispense a test strip, a user opens the lid 504 of the storage container 502. The opening of the lid 504 causes the slider arms 512 to rotate up and out of the storage container 502. The slider arms 512 are guided by cooperation of the guide bosses 536 and the slots in the slider arms 512 along a predetermined path. The second ends 520 of the slider arms 512 pull the first linkage members 514, which, in turn, pull the second linkage members 516. The second linkage members 516 travel substantially vertically up insider the storage container 502 due to the cooperation of the guide members 528 and guide rails and is raised up to a dispensing position. Since the lower contacting member 534 is located under a test strip, it raises and dispenses the test strip. Once the second linkage members 516 reach the dispensing position, a user may grasp the test strip and remove the dispensed test strip. The slider arms 512 and the first and second linkage members 514, 516 may be configured to completely dispense a test strip out of the storage container 502, or the test strip may be partially dispensed from the storage container 502 to expose the test strip so that a user may grasp the exposed test strip to completely withdraw the test strip from the storage container and use the test strip.

After the test strip has been dispensed, a user may then close the lid 504. Closing the lid 504 causes the linkage assembly 508 to return to its resting position. When the linkage assembly 508, and the second linkage members 516 in particular, reach the resting position, a biasing element urges the stack of test strips towards the side wall of the storage container 502 so that a new test strip is placed over the lower contacting member. Consequently, the storage container 502 is ready to dispense another test strip.

Sixth Exemplary Embodiment

Figure 21:
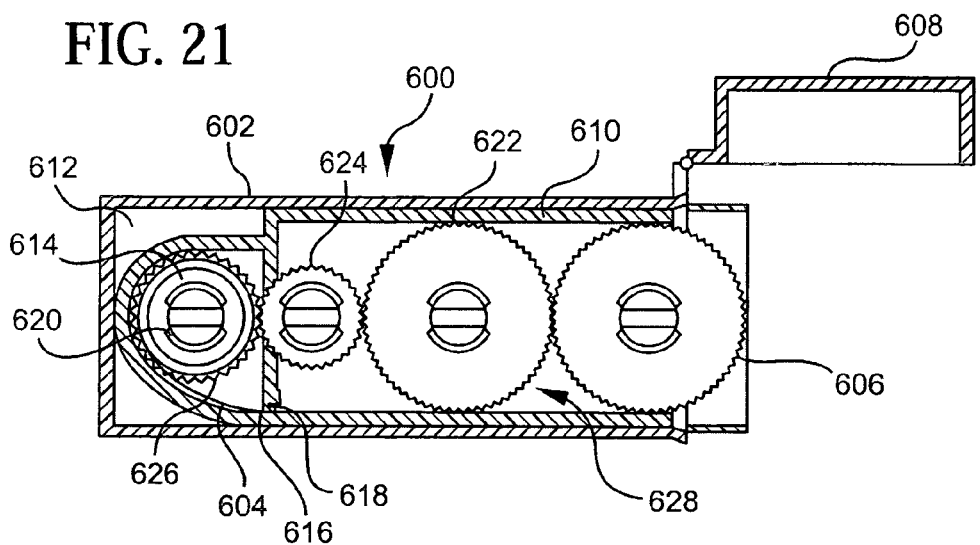
FIG. 21 is a sectional view of a storage vial for storing and dispensing test strips according to a sixth exemplary embodiment of the present invention.

Referring to FIG. 21, a storage vial 600 for storing and dispensing test strips according to a sixth exemplary embodiment of the present invention includes a storage container 602 configured to store a stack of test strips, a spiral pusher spring 604, and a thumbwheel 606 connected to the spiral pusher spring 604 by a gear train 628 so that rotation of the thumbwheel 606 causes the spring to dispense one test strip of the stack of test strips.

The storage container 602 is generally rectangular and forms a cavity 612 which is configured to receive a cartridge 610 for storing a stack of test strips. The storage container 602 may be formed of any suitable material, as previously discussed.

The storage vial 600 is provided with a lid 608 to prevent humidity and other environmental contaminants from entering the storage container 602. The lid 608 may be connected to the storage vial by any suitable type of hinge, such as a living hinge.

A cartridge 610 is inserted into the cavity in the storage container 602. The spiral pusher spring 604 and the associated gear train 628 are disposed in the cartridge 610. The cavity 612 in the cartridge 610 is configured to hold a stack of test strips, and a platform, as well as a biasing element, are located in the cavity to urge the stack of elements toward one wall of the cartridge 610. The cartridge 610 may be removable from the storage container 602 or permanently affixed thereto.

The spiral pusher spring 604 is wound around a cylindrical spring drum 614. A first end 616 of the spiral pusher spring 604 is disposed in a guide track 618 formed in the cartridge 610. A second end 620 of the spiral pusher spring 604 is fixed to the cylindrical spring drum 614. The first end 616 of the spiral pusher spring 604 is configured to contact the edge of a test strip. Accordingly, when the spring drum 614 is rotated, the first end 616 of the spiral pusher spring 604 is extended and moves along the guide track 618 to dispense a test strip.

In the illustrated embodiment, the gear train 628 comprises a thumbwheel driving gear 606, a first idler gear 622, a second idler gear 624, and a spring drum driving gear. 626. The thumbwheel driving gear 606 is partially exposed to the outside of the storage container 602 so that a user may manipulate the thumbwheel 606. The first and second idler gears 622, 624 engage the thumbwheel 606, and transmit a rotational force generated by the thumbwheel 606 to the spring drum driving gear 626. The gear train 628 may be configured with any desired gear ratios.

The method of using the storage vial 600 for storing and dispensing test strips according to the sixth exemplary embodiment of the invention will now be described. Initially, a stack of test strips is loaded into the cartridge 610, the spiral pusher spring 604 is retracted into an initial resting position, and the cartridge is inserted into the storage container 602. In the resting position, the spiral pusher spring 604 is retracted so that the end of the spring is located at the bottom of the storage container 602 and is underneath the lower edge of one edge of a test strip.

To dispense a test strip, a user rotates the exposed thumbwheel 606 in a dispensing direction. The rotational force of the thumbwheel 606 is transmitted to the spiral pusher spring 604 through the gear train 628. The spiral pusher spring 604 is extended and dispenses the test strip. The thumbwheel 606 may be rotated so that the test strip is completely dispensed out of the storage container 602, or the test strip may be partially dispensed from the storage container 602 to expose the test strip so that a user may grasp the exposed test strip to completely withdraw the test strip and use the test strip.

After the test strip has been dispensed, a user may then rotate the thumbwheel 606 in an opposite direction to the dispensing direction to return the spiral pusher spring 604 to its resting position. Alternatively, the inherent spring force of the spiral pusher spring 604 may cause it to return to its resting position automatically. When the spiral pusher spring 604 reaches the resting position, the biasing element urges the stack of test strips towards the spiral spring so that a new test strip is placed over the end of the pusher spring. Consequently, the storage container 602 is ready to dispense another test strip.

Seventh Exemplary Embodiment

Figure 22:
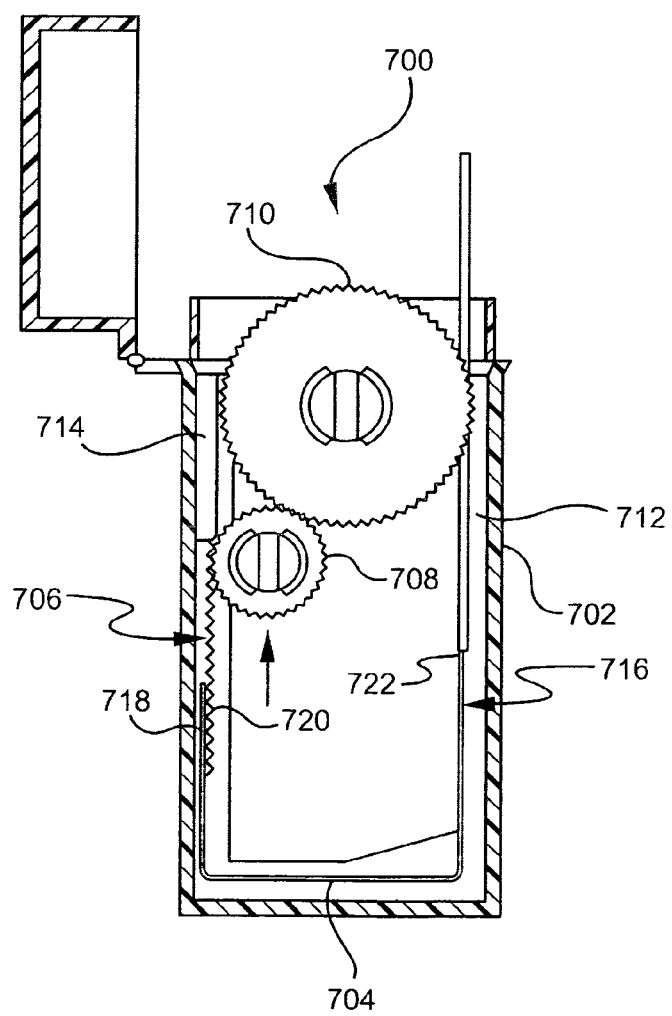
FIG. 22 is a sectional view of a storage vial for storing and dispensing test strips according to a seventh exemplary embodiment of the present invention.

Referring to FIG. 22, a storage vial 700 for storing and dispensing test strips according to a seventh exemplary embodiment of the present invention includes a storage container 702 configured to store a stack of test strips, a spring 704 configured to contact one test strip of the stack of test strips, a rack 706 connected to the spring 704, a pinion 708 engaging the rack 706, and a thumbwheel 710 engaging the pinion 708 so that rotation of the thumbwheel 710 displaces the rack 706 and causes the spring 704 to dispense the contacted test strip.

The storage container 702 and lid of this embodiment is generally configured the same as the storage container 702 and lid of the sixth exemplary embodiment.

A cartridge 712 is inserted into a cavity 714 in the storage container 702 502. The cartridge 712 has a cavity which is configured to hold a stack of test strips, and a platform, as well as a biasing element, are located in the cartridge 712 to urge the stack of test strips toward one wall of the cartridge 712. The cartridge 712 may be removable from the storage container 602 or permanently affixed thereto.

The spring 704 is disposed in a guide track 722 formed in the cartridge 712. A first end 716 of the spring 704 is guided by the guide track 722 and is configured to contact the edge of a test strip. A second end 718 of the spring 704 is fixed to the rack 706.

The rack 706 is linearly movable within the storage container 702. The rack 706 has a rack gear 720 located on one side of the rack.

A pinion gear 708 is rotatably disposed on the cartridge 712, and engages the rack gear 720.

The thumbwheel 710 is also rotatable disposed on the cartridge 712, and engages the pinion gear 708. Accordingly, when the thumbwheel 710 is rotated, the pinion gear 708 rotates, and the rack 706 translates linearly. Thus, the first end of the attached spring 704 is moved along the guide track 722.

The method of using the storage vial for storing and dispensing test strips according to the seventh exemplary embodiment of the invention will now be described. Initially, a stack of test strips is loaded into the cartridge 712, the pusher spring 704 and rack 706 are placed into an initial resting position, and the cartridge is inserted into the storage container 702. In the resting position, the rack 706 and pusher spring 704 are retracted so that the end of the spring 704 is located at the bottom of the storage container 702 and is underneath the lower edge of one edge of a test strip.

To dispense a test strip, a user rotates the exposed thumbwheel 710 in a dispensing direction. The rotational force of the thumbwheel 710 is transmitted to the pinion 708 gear, and the pinion gear 708 engages the rack 706 gear to translate the rotational force of the pinion gear 708 into linear movement of the rack 706. The linear movement of the rack 706 extends the pusher spring 704, and dispenses the test strip. The thumbwheel 710 may be rotated so that the test strip is completely dispensed out of the storage container 702, or the test strip may be partially dispensed from the storage container 702 to expose the test strip so that a user may grasp the exposed test strip to completely withdraw the test strip and use the test strip.

After the test strip has been dispensed, a user may then rotate the thumbwheel 710 in an opposite direction to the dispensing direction to return the pusher spring 704 to its resting position. Alternatively, the pusher spring can return to its resting position automatically. When the pusher spring 704 reaches the resting position, the biasing element urges the stack of test strips towards the pusher spring 704 so that a new test strip is placed over the end of the pusher spring 704. Consequently, the storage container 702 is ready to dispense another test strip.

Eighth Exemplary Embodiment

Figure 23:
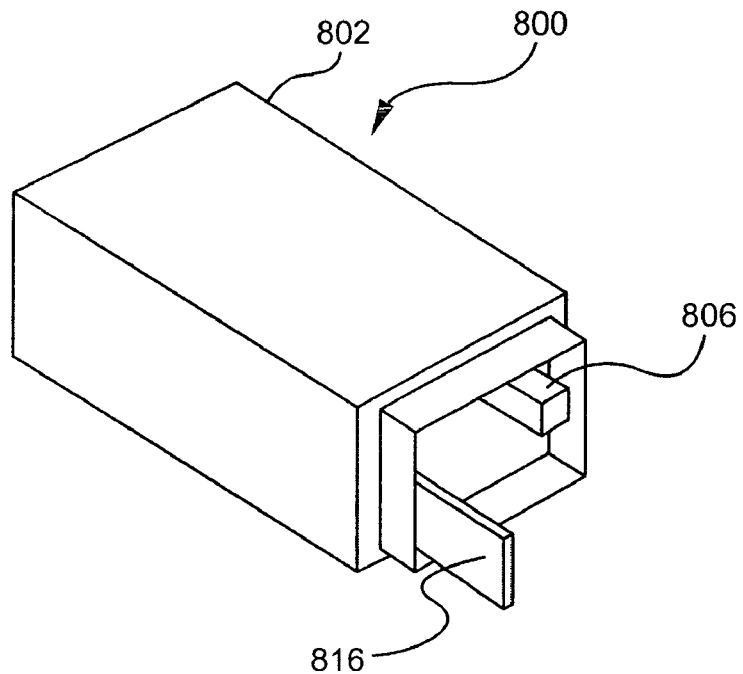
FIG. 23 is a perspective view of a storage vial for storing and dispensing test strips according to a eighth exemplary embodiment of the present invention.
Figure 24:
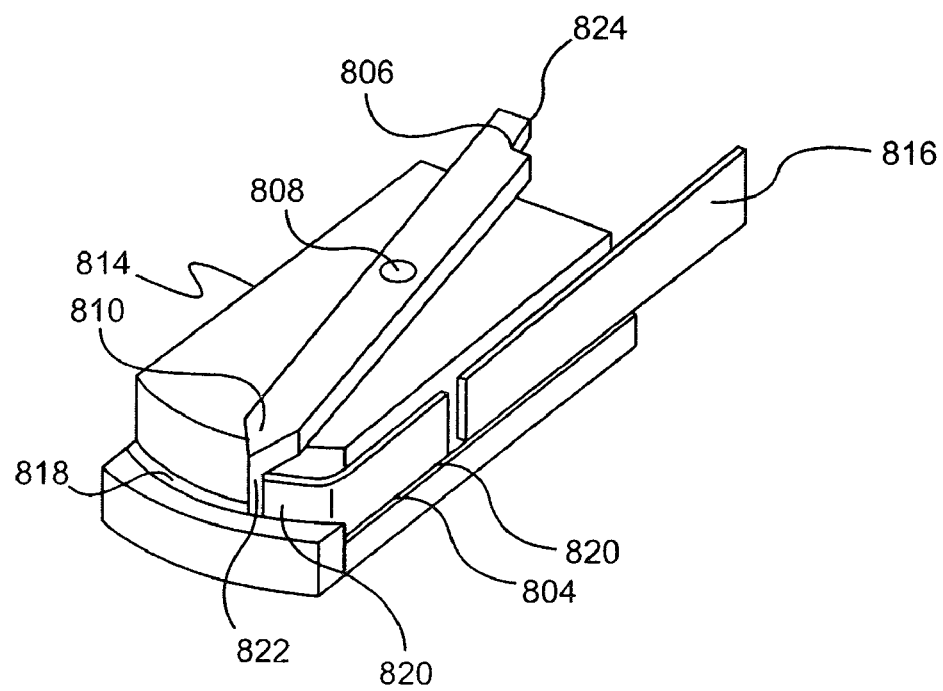
FIG. 24 is perspective view of a cartridge of the storage vial shown in FIG. 23.

Referring to FIGS. 23-24, a storage vial 800 for storing and dispensing test strips according to an eighth exemplary embodiment of the present invention includes a storage container 802 configured to store a stack of test strips rack, a spring 804 configured to contact one test strip of the stack of test strips, and a lever arm 806 that pivots about a pivot point 808. A first end 810 of the lever arm 806 is connected to the spring 804 to drive the spring 804 so that pivoting of the lever causes the spring 804 to dispense the contacted test strip.

The storage container 802 and lid (not shown) of this embodiment is generally configured the same as the storage container 602 and lid 608 of the sixth exemplary embodiment.

A cartridge 814 is inserted into a cavity in the storage container 802. A cavity in the cartridge 814 is configured to hold a stack of test strips, and a platform, as well as a biasing element, are located in the cavity to urge the stack of test strips toward one wall of the cartridge. The cartridge 814 may be removable from the storage container 802 or permanently affixed thereto.

The spring 804 is disposed in a guide track 818 formed by the cartridge and 814. The first end 820 of the spring 804 is guided by the guide track 818 and is configured to contact the edge of a test strip 816. A second end 822 of the spring 804 is fixed to a first end 810 of the lever arm 806.

The lever arm 806 is pivotably disposed about a pivot point 808 on the cartridge. The second end 824 of the lever arm 806 extends above the top end of the cartridge so that a user may manipulate the lever arm 806.

The method of using the storage vial 800 for storing and dispensing test strips according to the eighth exemplary embodiment of the invention will now be described. Initially, a stack of test strips is loaded into the cartridge 814, the lever arm 806 and the pusher spring 804 are placed into an initial resting position, and the cartridge is inserted into the storage container 802. In the resting position, the lever arm 806 is pivoted to one side of the storage container 802, and the pusher spring 804 is retracted so that the end of the spring 804 is located at the bottom of the storage container 802 and is underneath the lower edge of one edge of a test strip.

To dispense a test strip, a user presses the lever arm 806 to pivot the lever arm 806. The pivoting of the lever arm 806 causes the pusher spring 804 to extend along the guide track, and dispenses the test strip. The lever arm 806 is pivoted far enough for a user to grasp the test strip and remove the dispensed test strip.

After removing the test strip, a user may then pivot the lever arm 806 back to its initial resting position. Alternatively, the lever arm may return to its resting position automatically. When the lever arm 806 reaches the resting position, the biasing element urges the stack of test strips towards the pusher spring 804 so that a new test strip is placed over the end of the pusher spring 804. Consequently, the storage container 802 is ready to dispense another test strip.

While various embodiments have been chosen to illustrate the invention, it will be understood by those skilled in the art that various changes and modifications can be made therein without departing from the scope of the invention as defined in the appended claims.

What is claimed is:

1. An apparatus for storing and dispensing test strips, comprising:
   a container configured to store a stack of test strips; a wall at least partially enclosing the container;
   a roller rotatably disposed in the container, the roller adapted to contact one test strip of the stack of test strips;
   a thumbwheel for actuating the roller to dispense the one test strip from the container, the thumbwheel extending through the wall so as to be operable by a user; and
   a locking member allowing the thumbwheel to rotate in only one direction;
   a roller gear disposed on the roller; and
   an actuator gear disposed on the thumbwheel, the actuator gear engaging the roller gear so that the roller rotates when the thumbwheel rotates; and
   a motor for driving the thumbwheel.

2. The apparatus of claim 1, wherein the roller comprises rubber bonded to a roller insert.

3. The apparatus of claim 1, further comprising a biasing element for urging the stack of test strips stored in the storage container into contact with the roller.

4. An apparatus for storing and dispensing test strips, comprising:
   means for storing a stack of test strips;
   means for at least partially enclosing the means for storing the stack of test strips;
   means for contacting one test strip of the stack of test strips, wherein the contacting means comprises a roller;
   thumbwheel for actuating the contacting means to dispense the contacted test strip, the thumbwheel extending through the means for at least partially enclosing so as to be operable by a user;

means for allowing the thumbwheel to rotate in only one direction;

a roller gear disposed on the roller; and an actuator gear disposed on the thumbwheel, the actuator gear engaging the roller gear so that the roller rotates when the thumbwheel rotates; and means for driving the thumbwheel.

5. The apparatus of claim 4, wherein the roller comprises rubber bonded to a roller insert.

6. The apparatus of claim 4, wherein the contacting means contacts an edge of one test strip of the stack of test strips.

7. The apparatus of claim 4, further comprising means for urging the stack of test strips into a position such that the contacting means contacts said one test strip of the stack of test strips.

* * * * *